US00PP31237P2

(12) United States Plant Patent
van Rosmalen

(10) Patent No.: US PP31,237 P2
(45) Date of Patent: Dec. 17, 2019

(54) ***HYDRANGEA* PLANT NAMED 'HYLV02'**

(50) Latin Name: *Hydrangea paniculata*
Varietal Denomination: HYLV02

(71) Applicant: Nick van Rosmalen, Velp (NL)

(72) Inventor: Nick van Rosmalen, Velp (NL)

( * ) Notice: Subject to any disclaimer, the term of this patent is extended or adjusted under 35 U.S.C. 154(b) by 0 days.

(21) Appl. No.: 16/350,730

(22) Filed: Dec. 27, 2018

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hydrangea* plant named 'HYLV02', characterized by its compact, upright to somewhat spreading and mounded plant habit; moderately vigorous to vigorous growth habit and moderate growth rate; freely branching habit with strong and sturdy stems; freely and uniformly flowering habit; compact and dense panicle-type inflorescences with numerous light green to white-colored sterile flowers that become light red purple in color with development; and good landscape performance.

2 Drawing Sheets

Botanical designation: *Hydrangea paniculata.*
Cultivar denomination: 'HYLV02'.

BACKGROUND OF THE INVENTION

The present invention relates to a new and distinct cultivar of *Hydrangea* plant, botanically known as *Hydrangea paniculata*, commercially referred to as a paniculate-type *Hydrangea* and hereinafter referred to by the name 'HYLV02'.

The new *Hydrangea* plant is a product of a planned breeding program conducted by the Inventor in Velp and Reeuwijk, The Netherlands. The objective of the breeding program was to create new compact and freely-branching *Hydrangea* plants with strong sturdy stems, large inflorescences with numerous attractive sterile flowers and good postproduction longevity.

The new *Hydrangea* plant originated from an open-pollination made by the Inventor during the summer of 2012 in Velp, The Netherlands, of *Hydrangea paniculata* 'Phantom', not patented, as the female, or seed, parent with an unknown selection of *Hydrangea paniculata* as the male, or pollen, parent. The new *Hydrangea* plant was discovered and selected by the Inventor as a single flowering plant from within the progeny of the stated open-pollination in a controlled greenhouse environment in Reeuwijk, The Netherlands in August, 2014.

Asexual reproduction of the new *Hydrangea* plant by vegetative tip cuttings in a controlled environment in Reeuwijk, The Netherlands since August, 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HYLV02'. These characteristics in combination distinguish 'HYLV02' as a new and distinct *Hydrangea* plant:

1. Compact, upright to somewhat spreading and mounded plant habit.
2. Moderately vigorous to vigorous growth habit and moderate growth rate.
3. Freely branching habit with strong and sturdy stems.
4. Freely and uniformly flowering habit.
5. Compact and dense panicle-type inflorescences with numerous light green to white-colored sterile flowers that become light red purple in color with development.
6. Good landscape performance.

Plants of the new *Hydrangea* can be compared to plants of the female parent selection. Plants of the new *Hydrangea* differ primarily from plants of the female parent selection in the following characteristics:

1. Plants of the new *Hydrangea* are more compact than plants of the female parent selection.
2. Plants of the new *Hydrangea* have shorter lateral branches than plants of the female parent selection.
3. Inflorescences of plants of the new *Hydrangea* are more compact and denser than inflorescences of plants of the female parent selection.

Plants of the new *Hydrangea* can be compared to plants of the *Hydrangea paniculata* 'Limelight', disclosed in U.S. Plant Pat. No. 12,874. In side-by-side comparisons, plants of the new *Hydrangea* differ primarily from plants of 'Limelight' in the following characteristics:

1. Plants of the new *Hydrangea* are more compact than plants of 'Limelight'.
2. Plants of the new *Hydrangea* are more freely branching than plants of 'Limelight'.

3. Plants of the new *Hydrangea* have shorter lateral branches than plants of 'Limelight'.
4. Plants of the new *Hydrangea* are more freely flowering than plants of 'Limelight'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'HYLV02' grown in a container.

The photograph at the top left of the second sheet is a close-up view of a typical developing inflorescence of 'HYLV02'.

The photograph at the right top of the second sheet is a close-up view of typical developed inflorescences of 'HYLV02'.

The photograph at the bottom of the second sheet is a close-up view of typical leaves of 'HYLV02'.

DETAILED BOTANICAL DESCRIPTION

Plants used in the aforementioned photographs and in the following description were grown during the summer and early autumn in 21-cm containers in an outdoor nursery in Reeuwijk, The Netherlands and under cultural practices typical of commercial *Hydrangea* production. During the production of the plants, day temperatures ranged from about 16° C. to 25° C. and night temperatures ranged from about averaged 5° C. to 16° C. Plants of the new *Hydrangea* were two years old when the photographs and description were taken. In the following description, color references are made to The Royal Horticultural Society Colour Chart, 2015 Edition, except where general terms of ordinary dictionary significance are used.

Botanical description: *Hydrangea paniculata* 'HYLV02'.

Parentage:

*Female, or seed, parent.*—*Hydrangea paniculata* 'Phantom', not patented.

*Male, or pollen, parent.*—Unknown selection of *Hydrangea paniculata*, not patented.

Propagation:

*Type cutting.*—By vegetative tip cuttings.

*Time to initiate roots, summer.*—About 16 days at temperatures about 20° C. to 30° C.

*Time to produce a rooted young plant, summer.*—About four months at temperatures about 20° C. to 30° C.

*Root description.*—Medium in thickness to thick, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, upright to spreading and rounded plant habit; overall plant shape, narrowly obovate; strong and sturdy stems; moderately vigorous to vigorous growth habit and moderate growth rate.

*Plant height.*—About 47.5 cm.

*Plant diameter or area of spread.*—About 42.9 cm.

Lateral branch description:

*Branching habit.*—Freely branching habit; when pinched, about eleven lateral branches develop per plant.

*Length.*—About 30.5 cm.

*Diameter.*—About 4 mm.

*Internode length.*—About 3.5 cm.

*Texture.*—Smooth, glabrous; fully developed, woody.

*Aspect.*—Upright to about 50° from vertical.

*Strength.*—Strong, sturdy.

*Color, when developing.*—Close to 174B.

*Color, developed.*—Close to between 152A and N199A; when woody, close to 199B and 200D.

*Lenticels.*—Density: Sparse to medium. Size: About 1.5 mm by 0.75 mm. Color: Developing stems, close to N170D; developed stems, close to 199D.

Leaf description:

*Arrangement.*—Opposite, simple.

*Length.*—About 7.7 cm.

*Width.*—About 4.1 cm.

*Shape.*—Ovate to elliptic.

*Apex.*—Apiculate.

*Base.*—Obtuse.

*Margin.*—Serrate.

*Texture, upper and lower surfaces.*—Sparsely to moderately pubescent; slightly rugose.

*Venation pattern.*—Pinnate.

*Color.*—Developing leaves, upper surface: Close to between 137B and 143A. Developing leaves, lower surface: Close to 138B. Fully developed leaves, upper surface: Close to between NN137A and 147A; venation, close to 144A. Fully developed leaves, lower surface: Close to 147A; venation, close to 150D.

*Petioles.*—Length: About 1.3 cm. Diameter: About 2 mm. Texture and luster, upper and lower surfaces: Sparsely pubescent; matte. Color, upper surface: Close to 178B. Color, lower surface: Close to 152D.

Flower description:

*Flower type and habit.*—Showy sterile flowers and small inconspicuous fertile flowers arranged on panicle-type terminal panicles; panicles conical in shape, compact and dense; flowers face upright to outwardly depending on their position in the inflorescence.

*Fragrance.*—None detected.

*Natural flowering season.*—Early flowering habit, plants begin flowering about 70 days after planting; flowering begins in the midsummer and is continuous until late summer in The Netherlands.

*Flower longevity.*—Fertile flowers last about five days on the plant, fertile flowers not persistent; sterile flowers last about six weeks on the plant, sterile flowers persistent.

*Quantity of flowers.*—Freely flowering habit; about 75 fertile flowers per panicle and about 160 sterile flowers per panicle.

*Panicle height.*—About 14.1 cm.

*Panicle diameter.*—About 12.8 cm.

*Fertile flower buds.*—Length: About 3 mm. Diameter: About 3 mm. Shape: Obovate. Color: Close to 145C to 145D; towards the apex, tinged with close to 65A; immature calyx, close to 148D.

*Sterile flower buds*.—Length: About 6 mm. Diameter: About 8 mm. Shape: Cup-shaped. Color: Close to between 150D and 160D.

*Fertile flower diameter*.—About 7 mm.

*Fertile flower depth* (*height*).—About 6 mm.

*Sterile flower diameter*.—About 3.5 cm.

*Sterile flower depth* (*height*).—About 1 cm.

*Petals, fertile flowers*.—Quantity and arrangement: Four or five in a single whorl. Length: About 3.5 mm. Width: About 2 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D. When opening and fully opened, lower surface: Close to NN155D.

*Petals, sterile flowers*.—Quantity and arrangement: Four in a single whorl. Length: About 3 mm. Width: About 1.5 mm. Shape: Ovate, concave. Apex: Acute. Base: Cuneate. Margin: Entire. Texture and luster, upper and lower surfaces: Smooth, glabrous; matte. Color: When opening, upper surface: Close to NN155D; towards the apex, tinged with close to 65B. When opening, lower surface: Close to NN155B; towards the apex, tinged with close to 64D. Fully opened, upper surface: Close to NN155D. Fully opened, lower surface: Close to NN155B; towards the apex, slightly tinged with close to 64D.

*Sepals, fertile flowers*.—Quantity and arrangement: Five in a single whorl. Length: About 1 mm. Width: About 1.25 mm. Shape: Roughly deltoid. Apex: Acuminate. Base: Broadly cuneate. Margin: Entire. Texture and luster, upper and lower surfaces: Smooth, glabrous; matte. Color: When opening, upper and lower surfaces: Close to 157A. Fully opened, upper and lower surfaces: Close to 157A.

*Sepals, sterile flowers*.—Quantity and arrangement: Four in a single whorl. Length: About 1.8 cm. Width: About 1.2 cm. Shape: Ovate to narrowly ovate. Apex: Obtuse. Base: Cuneate. Margin: Finely serrate. Texture and luster, upper and lower surfaces: Smooth, glabrous; matte. Color: When opening, upper surface: Close to between 150D and 155A. When opening, lower surface: Close to 155A. Fully opened, upper and lower surfaces: Close to between 150D and 155A; color becoming closer to 63C and 186D with development.

*Pedicels, fertile flowers*.—Length: About 1 mm. Diameter: About 0.75 mm. Strength: Moderately strong. Aspect: About 20° from vertical. Texture and luster: Densely pubescent; matte. Color: Close to 157B.

*Pedicels, sterile flowers*.—Length: About 1.7 cm. Diameter: About 0.8 mm. Strength: Moderately strong. Aspect: About 55° from branch axis. Texture and luster: Moderately pubescent; matte. Color: Close to 157A.

*Reproductive organs, fertile flowers*.—Stamens: Quantity per flower: About ten. Filament length: About 5 mm. Filament color: Close to NN155D. Anther length: About 0.75 mm. Anther shape: Oblong. Anther color: Close to 157A. Pollen amount: Moderate. Pollen color: Close to 156A. Pistils: Pistil quantity per flower: Three. Pistil length: About 1 mm. Stigma shape: Club-shaped. Stigma color: Close to 157D. Style length: About 1 mm. Style color: Close to 157D. Ovary color: Close to 145D.

*Reproductive organs, sterile flowers*.—Stamens: Quantity per flower: About eight. Filament length: About 3 mm. Filament color: Close to NN155D. Anther length: About 0.75 mm. Anther shape: Oblong. Anther color: Close to 157A. Pollen amount: Moderate. Pollen color: Close to 156A. Pistils: To date, pistil development has not been observed on sterile flowers of plants of the new *Hydrangea*.

*Seeds*.—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Landscape performance: Plants of the new *Hydrangea* have been observed to tolerate wind and rain and to be suitable for USDA Hardiness Zones 5 through 9.

It is claimed:

1. A new and distinct *Hydrangea* plant named 'HYLV02' as illustrated and described.

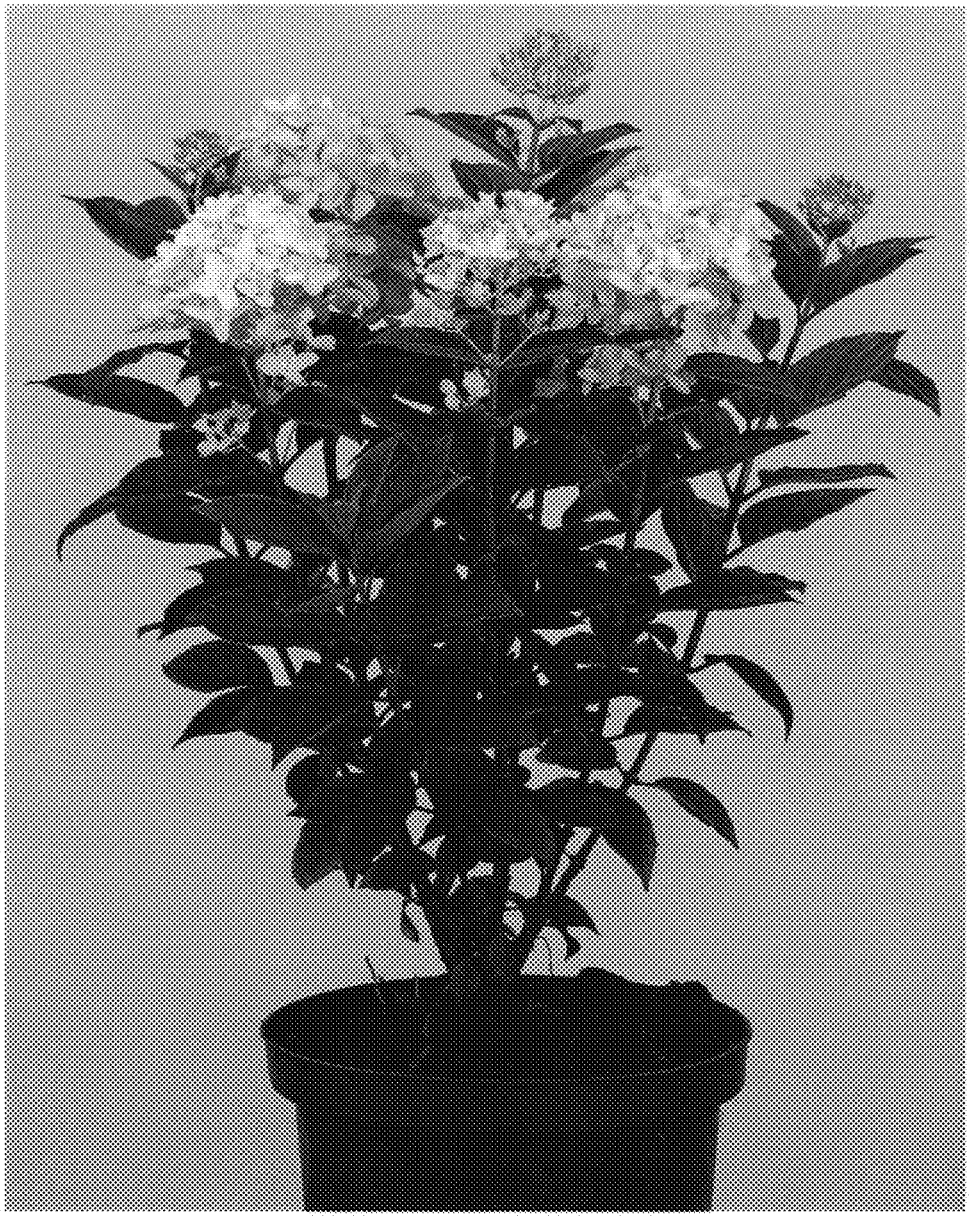

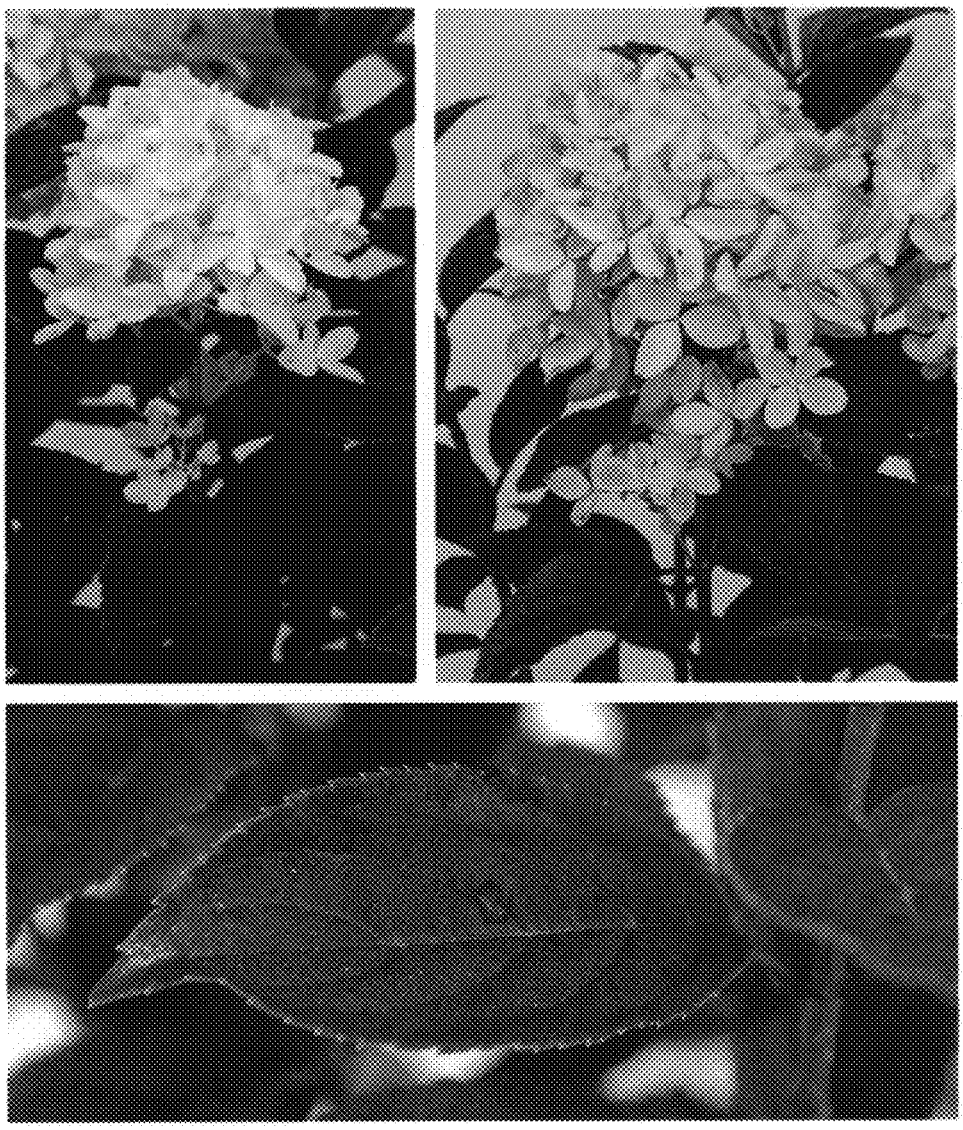

* * * * *